United States Patent [19]

Zedda et al.

[11] Patent Number: 6,114,420

[45] Date of Patent: Sep. 5, 2000

[54] TRIAZINE DERIVATIVES CONTAINING 2,2, 6,6-TETRAMETHYL-4-PIPERIDYL GROUPS

[75] Inventors: Alessandro Zedda, Casalecchio di Reno; Gianluca Ferri, Anzola Emilia, both of Italy

[73] Assignee: Ciba Specialty Chemicals Corporation, Tarrytown, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 09/084,681

[22] Filed: May 26, 1998

[30] Foreign Application Priority Data

May 27, 1997 [EP] European Pat. Off. .............. 97810332

[51] Int. Cl.$^7$ ...................... C07D 401/14; C08K 5/3435
[52] U.S. Cl. .......................... 524/100; 544/198; 544/209
[58] Field of Search ..................................... 544/198, 209, 544/219; 524/100

[56] References Cited

U.S. PATENT DOCUMENTS

| | | | |
|---|---|---|---|
| 4,086,204 | 4/1978 | Cassandrini et al. ................... | 260/45.8 |
| 4,234,707 | 11/1980 | Rody et al. .............................. | 525/437 |
| 4,331,586 | 5/1982 | Hardy ...................................... | 525/186 |
| 4,335,242 | 6/1982 | Wiezer et al. ........................... | 544/198 |
| 4,459,395 | 7/1984 | Cantatore ................................. | 524/100 |
| 4,492,791 | 1/1985 | Orban et al. ............................. | 544/198 |
| 4,526,972 | 7/1985 | Speranza et al. ........................ | 546/191 |
| 4,847,380 | 7/1989 | Speranza et al. ........................ | 546/190 |
| 5,198,546 | 3/1993 | Borzatta et al. ......................... | 544/198 |
| 5,455,347 | 10/1995 | Maskawa et al. ........................ | 544/198 |

FOREIGN PATENT DOCUMENTS

| | | |
|---|---|---|
| 0033663 | 8/1981 | European Pat. Off. . |
| 0053775 | 6/1982 | European Pat. Off. . |
| 0354185 | 2/1990 | European Pat. Off. . |
| 0357223 | 3/1990 | European Pat. Off. . |
| 0377324 | 7/1990 | European Pat. Off. . |
| 0462069 | 12/1991 | European Pat. Off. . |
| 0488502 | 6/1992 | European Pat. Off. . |
| 0627428 | 12/1994 | European Pat. Off. . |
| 61-176662 | 8/1986 | Japan . |

*Primary Examiner*—Richard L. Raymond
*Assistant Examiner*—Deepak R. Rao
*Attorney, Agent, or Firm*—Luther A.R. Hall; Kevin T. Mansfield; Tyler A. Stevenson

[57] ABSTRACT

A compound of the formula (I)

wherein n is an integer from 1 to 4; the radicals $R_1$ are for example a group of the formula $R_3$ is for example hydrogen, $C_1$–$C_8$ alkyl or $C_5$–$C_{12}$ cycloalkoxy; Z and $R_2$ are for example a group $$\text{—CH—CH}_2\text{—} \quad \text{or} \quad \text{—CH—(CH}_2)_2\text{—};$$
$$\underset{CH_3}{|} \qquad\qquad \underset{C_2H_5}{|}$$

the radicals A and E are, for example, independently of one another $-N(R_{11})(R_{12})$ or a group of the formula $R_{11}$ and $R_{12}$ are for example $C_1$–$C_{12}$ alkyl; $R_{13}$ has for example one of the meanings given for $R_3$; $E^*$ has for example one of the meanings given for A or is a group of the formula The compounds of the formula (I) are useful as light stabilizers, heat stabilizers and oxidation stabilizers for organic materials, in particular synthetic polymers such as polyolefins.

13 Claims, No Drawings

TRIAZINE DERIVATIVES CONTAINING 2,2, 6,6-TETRAMETHYL-4-PIPERIDYL GROUPS

This invention relates to triazine derivatives containing 2,2,6,6-tetramethyl-4-piperidyl groups, to their use as light stabilizers, heat stabilizers and oxidation stabilizers for organic materials, particularly synthetic polymers, and to the organic materials thus stabilized.

The stabilization of synthetic polymers with derivatives of 2,2,6,6-tetramethylpiperidine has been described for example in U.S. Pat. No. 4,086,204, U.S. Pat. No. 4,234,707, U.S. Pat. No. 4,331,586, U.S. Pat. No. 4,335,242, U.S. Pat. No. 4,459,395, U.S. Pat. No. 4,492,791, U.S. Pat. No. 4,847,380, U.S. Pat. No. 5,198,546, U.S. Pat. No. 5,455,347, EP-A-53 775, EP-A-357 223, EP-A-377 324 and EP-A-488 502.

This invention relates in particular to a compound of the formula (I)

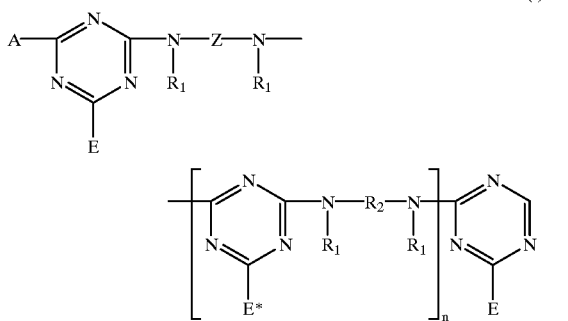

(I)

wherein n is an integer from 1 to 4;

the radicals $R_1$ are independently of one another hydrogen, $C_1$–$C_8$alkyl, $C_5$–$C_{12}$cycloalkyl unsubstituted or substituted by 1, 2 or 3 $C_1$–$C_4$alkyl; or a group of the formula (II),

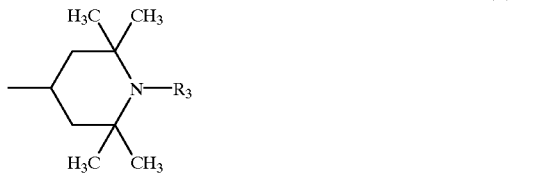

(II)

with the proviso that at least one of the radicals $R_1$ is a group of the formula (II);

$R_3$ is hydrogen, $C_1$–$C_8$alkyl, O ., —OH, —CH$_2$CN, $C_1$–$C_{18}$alkoxy, $C_5$–$C_{12}$cycloalkoxy, $C_3$–$C_6$alkenyl, $C_7$–$C_9$phenylalkyl unsubstituted or substituted on the phenyl by 1, 2 or 3 $C_1$–$C_4$alkyl; or $C_1$–$C_8$acyl;

Z is a group of the formula (IIIa) or (IIIb);

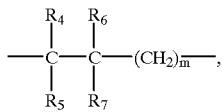

(IIIa)

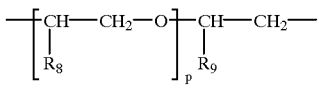

(IIIb)

$R_4$, $R_8$ and $R_9$ are independently of one another $C_1$–$C_4$alkyl or $C_5$–$C_{12}$cycloalkyl unsubstituted or substituted by 1, 2 or 3 $C_1$–$C_4$alkyl;

$R_5$, $R_6$ and $R_7$ are independently of one another hydrogen or $C_1$–$C_4$alkyl;

m is zero or an integer from 1 to 6;

p is 1 or 2;

$R_2$ has one of the meanings given for Z or is $C_2$–$C_{12}$alkylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by 1,4-piperazinediyl, —O— or >N—X$_1$ with X$_1$ being $C_1$–$C_{12}$acyl or ($C_1$–$C_8$alkoxy)carbonyl or having one of the meanings given for $R_1$ except hydrogen;

the radicals A are independently of one another —OR$_{10}$, —N(R$_{11}$)(R$_{12}$) or a group of the formula (IV);

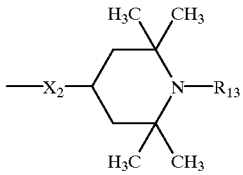

(IV)

$R_{10}$, $R_{11}$ and $R_{12}$ are independently of one another hydrogen, $C_1$–$C_{12}$alkyl, $C_5$–$C_{12}$cycloalkyl unsubstituted or substituted by 1, 2 or 3 CG-$C_4$alkyl; $C_3$–$C_{12}$alkenyl, phenyl unsubstituted or substituted by 1, 2 or 3 $C_1$–$C_4$alkyl or $C_1$–$C_4$alkoxy; $C_7$–$C_9$phenylalkyl unsubstituted or substituted on the phenyl by 1, 2 or 3 $C_1$–$C_4$alkyl or $C_1$–$C_4$alkoxy; tetrahydrofurfuryl or $C_2$–$C_4$alkyl substituted in the 2, 3 or 4 position by —OH, $C_1$–$C_8$alkoxy, di($C_1$–$C_4$alkyl)amino or a group of the formula (V)

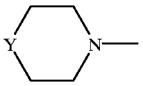

(V)

with Y being —O—, —CH$_2$—, —CH$_2$CH$_2$— or >N—CH$_3$; or —N(R$_{11}$)(R$_{12}$) is additionally a group of the formula (V);

$R_{13}$ has one of the meanings given for $R_3$;

$X_2$ is —O— or >N—R$_{14}$;

$R_{14}$ is hydrogen, $C_1$–$C_{12}$alkyl, $C_5$–$C_{12}$cycloalkyl unsubstituted or substituted by 1, 2 or 3 $C_1$–$C_4$alkyl; $C_7$–$C_9$phenylalkyl unsubstituted or substituted on the phenyl by 1, 2 or 3 $C_1$–$C_4$alkyl or $C_1$–$C_4$alkoxy; tetrahydrofurfuryl, a group of the formula (II) or $C_2$–$C_4$alkyl substituted in the 2, 3 or 4 position by —OH, $C_1$–C8alkoxy, di($C_1$–$C_4$alkyl)amino or a group of the formula (V);

the radicals E have independently of one another one of the meanings given for A; and E* has one of the meanings given for A or is a group of the formula (VI)

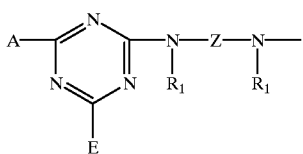
(VI)

with A, E, $R_1$ and Z being as defined above;
with the proviso that, when n is 2, 3 or 4, each of the radicals E*, $R_1$ and $R_2$ in the repetitive units can have the same or a different meaning.

Each of the radicals E*, $R_1$ and $R_2$ has preferably the same meaning in the several repetitive units of the formula (I).

Examples of alkyl containing not more than 12 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl and dodecyl. $R_{11}$, $R_{12}$ and $R_{14}$ are preferably $C_1$–$C_8$alkyl, in particular $C_1$–$C_4$alkyl. $R_4$ is preferably methyl or ethyl. One of the preferred meanings of $R_1$ is methyl.

An example of $C_2$–$C_4$alkyl substituted by —OH is 2-hydroxyethyl.

Examples of $C_2$–$C_4$alkyl substituted by $C_1$–$C_8$alkoxy, preferably by $C_1$–$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$–$C_4$alkyl substituted by di($C_1$–$C_4$alkyl) amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

The group of the formula (V) is preferably

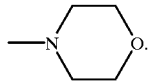

Preferred examples of $C_2$–$C_4$alkyl substituted by a group of the formula (V) are groups of the formula

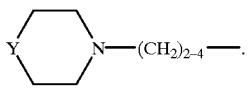

The group

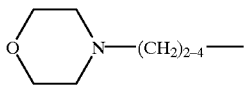

is particularly preferred.

Examples of alkoxy containing not more than 18 carbon atoms are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. $C_6$–$C_{12}$Alkoxy, in particular heptoxy and octoxy, is one of the preferred meanings of $R_3$.

Examples of $C_5$–$C_{12}$cycloalkyl which is unsubstituted or substituted by 1, 2 or 3 $C_1$–$C_4$alkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Unsubstituted or substituted cyclohexyl is preferred.

Examples of $C_5$–$C_{12}$cycloalkoxy are cyclopentoxy, cyclohexoxy, cycloheptoxy, cyclooctoxy, cyclodecyloxy, cyclododecyloxy and methylcyclohexoxy. $C_5$–$C_8$Cycloalkoxy, in particular cyclopentoxy and cyclohexoxy, is preferred.

Examples of alkenyl containing not more than 12 carbon atoms are allyl, 2-methylallyl, butenyl, hexenyl, undecenyl and dodecenyl. Alkenyls in which the carbon atom in the 1-position is saturated are preferred, and allyl is particularly preferred.

Examples of phenyl substituted by 1, 2 or 3 $C_1$–$C_4$alkyl or $C_1$–$C_4$alkoxy are methylphenyl, dimethylphenyl, trimethylphenyl, t-butylphenyl, di-t-butylphenyl, 3,5-di-t-butyl-4-methylphenyl, methoxyphenyl, ethoxyphenyl and butoxyphenyl.

Examples of $C_7$–$C_9$phenylalkyl which is unsubstituted or substituted on the phenyl by 1, 2 or 3 $C_1$–$C_4$alkyl or $C_1$–$C_4$alkoxy are benzyl, methylbenzyl, methoxybenzyl, dimethylbenzyl, trimethylbenzyl, t-butylbenzyl and 2-phenylethyl. Benzyl is preferred.

Examples of acyl (aliphatic, cycloaliphatic or aromatic) containing not more than 12 carbon atoms are formyl, acetyl, propionyl, butyryl, pentanoyl, hexanoyl, heptanoyl, octanoyl and benzoyl. $C_1$–$C_8$Alkanoyl and benzoyl are preferred. Acetyl is especially preferred.

Examples of ($C_1$–$C_8$alkoxy)carbonyl are methoxycarbonyl, ethoxycarbonyl, propoxycarbonyl, butoxycarbonyl, pentoxycarbonyl, hexoxycarbonyl, heptoxycarbonyl, octoxycarbonyl, nonyloxycarbonyl, decyloxycarbonyl, undecyloxycarbonyl and dodecyloxycarbonyl.

Examples of alkylene containing not more than 12 carbon atoms are ethylene, propylene, trimethylene, tetramethylene, pentamethylene, hexamethylene, octamethylene, decamethylene and dodecamethylene. $R_2$ is for example $C_2$–$C_8$alkylene or $C_4$–$C_8$alkylene, in particular $C_2$–$C_6$alkylene, preferably hexamethylene.

An example of $C_5$–$C_7$cycloalkylene is cyclohexylene.

Examples of $C_4$–$C_{12}$alkylene interrupted by 1,4-piperazinediyl are

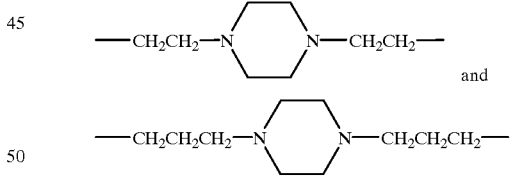

and

Examples of $C_4$–$C_{12}$alkylene interrupted by —O—, e.g. 1, 2 or 3 —O—, are 3-oxapentane-1,5-diyl, 4-oxaheptane-1,7-diyl, 3,6-dioxaoctane-1,8-diyl, 4,7-dioxadecane-1,10-diyl, 4,9-dioxadodecane-1,12-diyl, 3,6,9-trioxaundecane-1,11-diyl and 4,7,10-trioxatridecane-1,13-diyl.

Examples of $C_4$–$C_{12}$alkylene interrupted by >N—$X_1$ are —$CH_2CH_2CH_2$—N($X_1$)—$CH_2CH_2$—N($X_1$)—$CH_2CH_2CH_2$—, in particular —$CH_2CH_2CH_2$—N($CH_3$)—$CH_2CH_2$—N($CH_3$)—$CH_2CH_2CH_2$—.

An example of $C_5C_7$cycloalkylenedi($C_1$–$C_4$alkylene) is methylene-cyclohexylene-methylene.

Examples of $C_1$–$C_4$alkylenedi($C_5$–$C_7$cycloalkylene) are cyclohexylene-methylene-cyclohexylene and cyclohexylene-isopropylidene-cyclohexylene.

An example of phenylenedi($C_1$–$C_4$alkylene) is methylene-phenylene-methylene.

$R_3$ is preferably hydrogen, $C_1$–$C_4$alkyl, —OH, $C_6$–$C_{12}$alkoxy, $C_5$–$C_8$cycloalkoxy, allyl, benzyl or acetyl, in particular hydrogen, $C_1$–$C_4$alkyl or $C_5$–$C_8$cycloalkoxy, for example hydrogen, methyl or cyclohexyloxy.

Z is preferably a group of the formula (IIIa) with $R_5$, $R_6$ and $R_7$ being hydrogen.

m is preferably zero or 1.

$R_2$ and Z are preferably identical.

Compounds of the formula (I) which are preferred are those wherein the radicals $R_1$ are independently of one another hydrogen, $C_1$–$C_4$alkyl, $C_5$–$C_8$cycloalkyl unsubstituted or substituted by methyl; or a group of the formula (II) with the proviso that at least one of the radicals RI is a group of the formula (II);

$R_4$, $R_8$ and $R_9$ are independently of one another $C_1$–$C_4$alkyl or cyclohexyl;

$R_5$, $R_6$ and $R_7$ are hydrogen;

m is zero or an integer from 1 to 3;

$R_2$ has one of the meanings given for Z or is $C_2$–$C_8$alkylene, cyclohexylene, methylene-cyclohexylene-methylene, cyclohexylene-methylene-cyclohexylene or methylene-phenylene-methylene;

$R_{10}$, $R_{11}$ and $R_{12}$ are independently of one another hydrogen, $C_1$–$C_8$alkyl, $C_5$–$C_8$cycloalkyl unsubstituted or substituted by methyl; $C_3$–$C_8$alkenyl, phenyl unsubstituted or substituted by methyl; benzyl, tetrahydrofurfuryl or $C_2$–$C_3$alkyl substituted in the 2 or 3 position by —OH, $C_1$–$C_4$alkoxy, dimethylamino, diethylamino or 4-morpholinyl; or —N($R_{11}$)($R_{12}$) is additionally 4-morpholinyl;

$R_{14}$ is hydrogen, $C_1$–$C_8$alkyl, $C_5$–$C_8$cycloalkyl unsubstituted or substituted by methyl; benzyl, tetrahydrofurfuryl, a group of the formula (II) or $C_2$–$C_3$alkyl substituted in the 2 or 3 position by —OH, $C_1$–$C_4$alkoxy, dimethylamino, diethylamino or 4-morpholinyl.

Compounds of the formula (I) which are particularly preferred are those wherein the radicals $R_1$ are independently of one another hydrogen, $C_1$–$C_4$alkyl, cyclohexyl or a group of the formula (II) with the proviso that at least one of the radicals $R_1$ is a group of the formula (II);

Z is a group of the formula (IIIa);

$R_4$ is $C_1$–$C_4$ alkyl;

$R_5$, $R_6$ and $R_7$ are hydrogen;

m is zero or 1;

$R_2$ has one of the meanings given for Z or is $C_2$–$C_8$alkylene;

A is —N($R_{11}$)($R_{12}$) or a group of the formula (IV);

$R_{11}$ and $R_{12}$ are independently of one another hydrogen, $C_1$–$C_8$alkyl, cyclohexyl, phenyl, benzyl, tetrahydrofurfuryl, 2-hydroxyethyl or 2-methoxyethyl; or —N($R_{11}$)($R_{12}$) is additionally 4-morpholinyl;

$X_2$ is >N—$R_{14}$;

$R_{14}$ is hydrogen, $C_1$–$C_8$alkyl, cyclohexyl, benzyl, tetrahydrofurfuryl, a group of the formula (II), 2-hydroxyethyl or 2-methoxyethyl.

Compounds of the formula (I) which are of interest are those wherein n is 1 or 2;

the radicals $R_1$ are a group of the formula (II);

Z is a group $$-\underset{CH_3}{\underset{|}{CH}}-CH_2- \quad \text{or} \quad -\underset{C_2H_5}{\underset{|}{CH}}-(CH_2)_2-;$$

$R_2$ has one of the meanings given for Z;

$R_3$ is hydrogen, $C_1$–$C_4$alkyl or $C_5$–$C_8$cycloalkoxy;

A is —N($R_{11}$)($R_{12}$) or a group of the formula (IV);

$R_{11}$ and $R_{12}$ are independently of one another $C_1$–$C_4$alkyl;

$X_2$ is >N—$R_{14}$; and $R_{14}$ is $C_1$–$C_4$alkyl.

The compounds of the formula (I) may be prepared, for example, according to the methods shown in the following.

Method A:

When $R_2$ has the same meaning as Z and the radicals E and E* have the same meanings, a compound of the formula (VII)

(VII)

[chemical structure: Cl-triazine-N(R_1)-Z-N(R_1)-triazine(Cl)-[N-Z-N(R_1)-triazine(Cl)]_n-Cl with Cl substituents]

may be prepared, for example, by reaction of a compound of the formula (VII) with an appropriate molar amount of a compound of the formula (IX).

(VIII)

$$H-\underset{R_1}{\underset{|}{N}}-Z-\underset{R_1}{\underset{|}{N}}-H,$$

(IX)

[chemical structure: 2,4,6-trichlorotriazine]

In more detail, when n is 1, a compound of the formula (VII) may be prepared, for example, according to Scheme A-1.
Scheme A-1:
a) 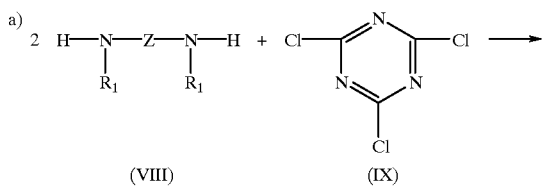
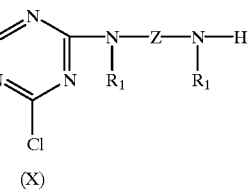
b) 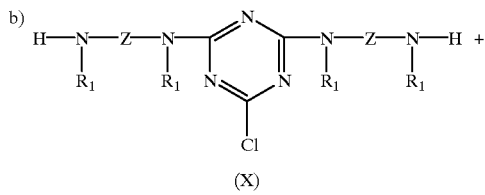
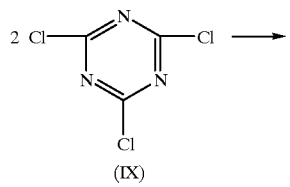
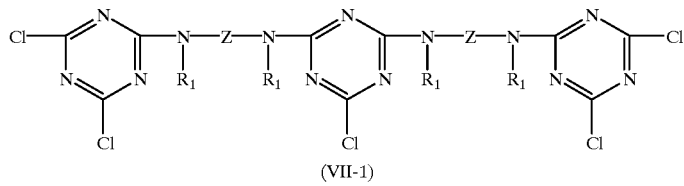
When n is 2, a compound of the formula (VII) may be prepared, for example, according to Scheme A-2.
Scheme A-2:
a) 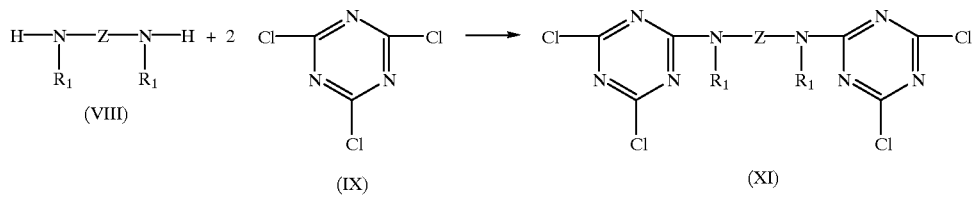

b)
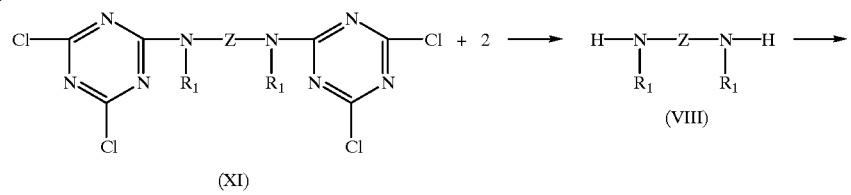
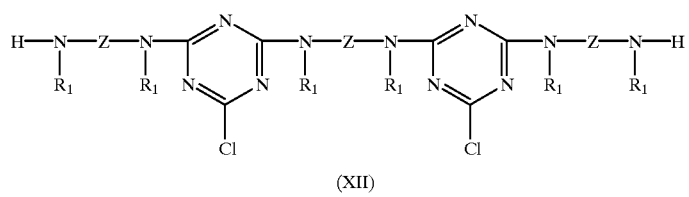
c)
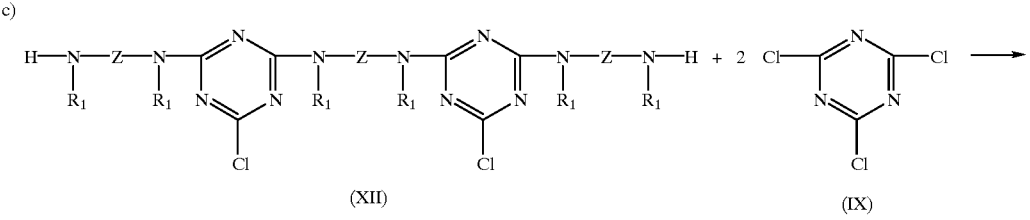
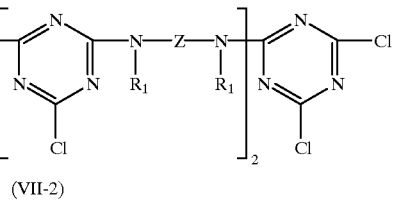
When n is 3, a compound of the formula (VII) may be prepared, for example, according to Scheme A-3.
Scheme A-3:
a)
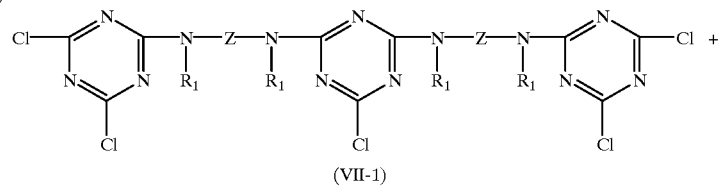
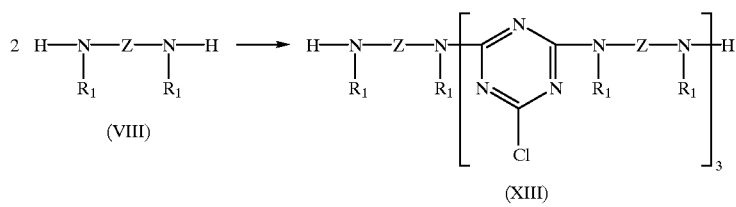
b)
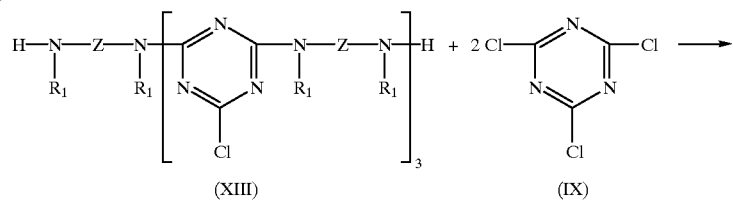

-continued

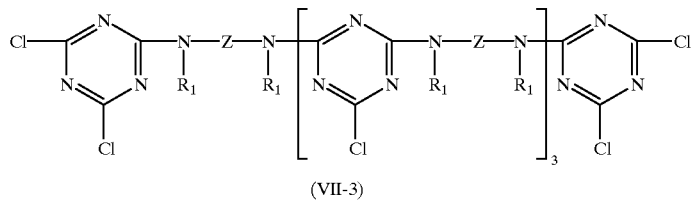

(VII-3)

When n is 4, a compound of the formula (VII) may be prepared, for example, according to Scheme A-4.

Scheme A-4:

a)

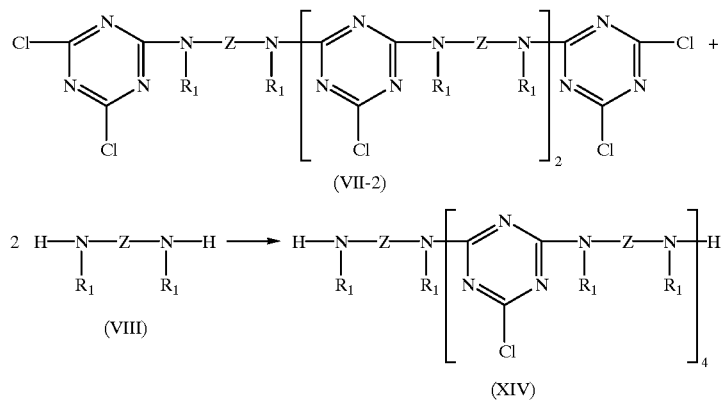

b)

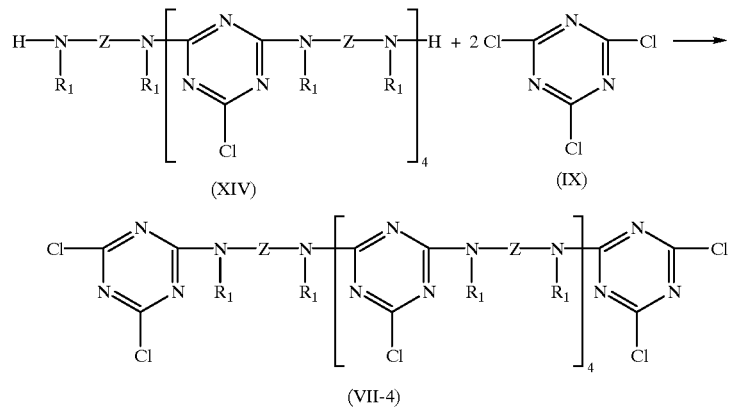

Thereafter, the compounds of the formulae (VII-1), (VII-2), (VII-3) and (VII-4) are caused to react with the appropriate molar amounts of the compounds of the formulae (XV) and/or (XVI)

A—H    (XV)

E—H    (XVI)

to obtain the corresponding compounds of the formula (I).

Method B:

When $R_2$ has the same meaning as Z, the radical E* is different from the radicals E and the radical E* is also different from the group of the formula (VI), the compounds of the formulae (X), (XII), (XIII) and (XIV), depending on the value of n=1, 2, 3 or 4, respectively, are first prepared according to METHOD A as described above.

Thereafter, these compounds are caused to react with the appropriate molar amounts of the compounds of the formula (XVII)

E*—H    (XVII)

to give the compounds of the formula (XVIII)

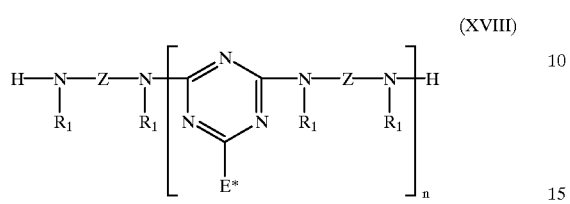
(XVIII)

with n being 1, 2, 3 or 4, respectively.

Then, the compounds of the formula (XVIII) are caused to react with the appropriate molar amounts of the compound of the formula (IX) or (XIX)

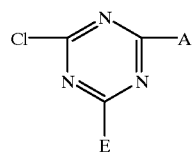
(XIX)

to obtain the corresponding compounds of the formula (XX) or (I).

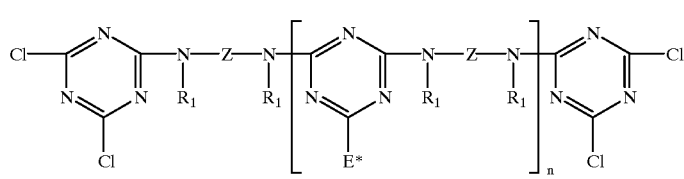
(XX)

with n being 1, 2, 3 or 4, respectively.

When the compounds of the formula (XX) are obtained, these compounds are subsequently caused to react with the appropriate molar amounts of the compounds of the formulae (XV) and/or (XVI) to give the corresponding compounds of the formula (I).

The compounds of the formula (XIX) may be prepared by using well know synthesis procedures, for example, reacting the compound of the formula (IX) with the appropriate molar amounts of the compounds of the formulae (XV) and/or (XVI).

Method C:

When $R_2$ has the same meaning as Z and the radical E* is a group of the formula VI, the compounds of the formulae (X), (XII), (XIII) and (XIV), depending on the value of n=1, 2, 3 or 4, respectively, are first prepared according to METHOD A as described above.

Thereafter, these compounds are caused to react with the appropriate molar amounts of the compounds of the formula (VIII) to give the compounds of the formula (XXI)

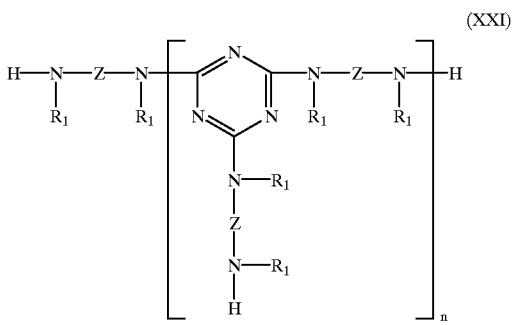
(XXI)

with n being 1, 2, 3 or 4, respectively.

Then, the compounds of the formula (XXI) are caused to react with the appropriate molar amounts of the compound of the formula (IX) or (XIX) to obtain the corresponding compounds of the formula (XXII) or (I).

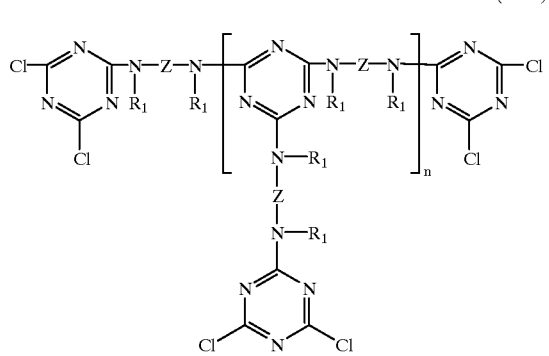
(XXII)

When the compounds of the formula (XXII) are obtained, these compounds are subsequently caused to react with the appropriate molar amounts of the compounds of the formulae (XV) and/or (XVI) to give the corresponding compounds of the formula (I).

Method D:

When $R_2$ is different from Z or at least one of the radicals $R_2$—in the recurring units (n=2, 3 or 4) of the compounds of the formula (I)—is different from Z, the compounds of the formula (XXIII)

(XXIII)

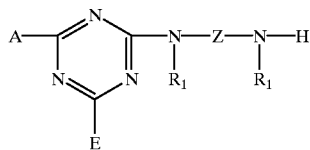

are first prepared by reacting the compounds of the formula (XIX) with the equivalent molar amounts or an excess of the compounds of the formula (XXIV).

(XXIV)

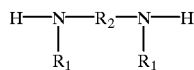

Thereafter, the compounds of the formula (XXIII) are caused to react with the appropriate molar amounts of the compounds of the formulae (XXV) and (XXIV)

(XXV)

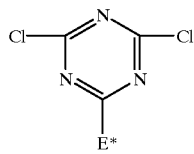

analogously to the method described for example in EP-A-782 994 to give the compounds of the formula (XXVI).

(XXVI)

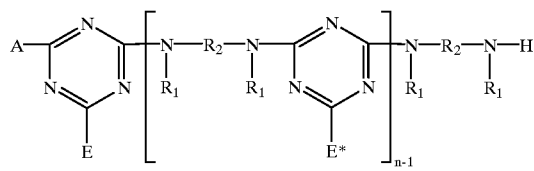

Subsequently, when E* has the same meaning as E, the compounds of the formula (XXVI) are caused to react with the appropriate molar amounts of the compounds of the formula (XXVII)

(XXVII)

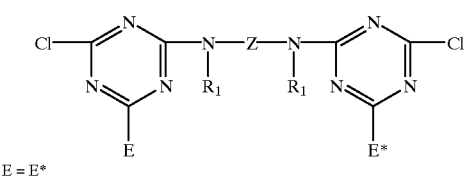

to give the compounds of the formula (XXVIII).

(XXVIII)

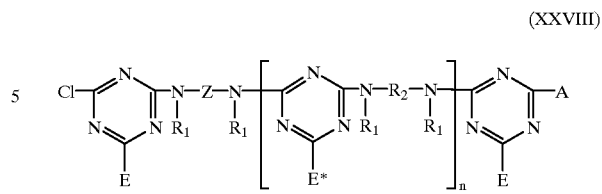

Then, the compounds of the formula (XXVIII) are caused to react with the appropriate molar amounts of the compounds of the formula (XV) to give the corresponding compounds of the formula (I).

When E* is different from E, the compounds of the formula (XXVI) are caused to react with the appropriate molar amounts of the compounds of the formula (XXV) to give the compounds of the formula (XXIX).

(XXIX)

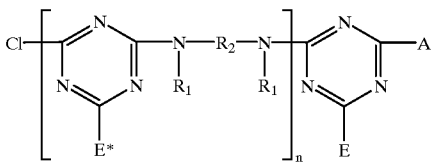

Thereafter, the compounds of the formula (XXIX) are caused to react with the appropriate molar amounts of the compounds of the formula (XXIII) to give the corresponding compounds of the formula (I).

Alternatively, the compounds of the formula (XXIX) are caused to react with the appropriate molar amounts of the compounds of the formula (VIII) and, thereafter, with the appropriate molar amounts of the compounds of the formula (XIX) to give the corresponding compounds of the formula (I).

Alternatively again, the compounds of the formula (XXIX) are caused to react with the appropriate molar amounts of the compounds of the formula (VIII) and, thereafter, with the appropriate molar amounts of the compound of the formula (IX) to give the compounds of the formula (XXX).

(XXX)

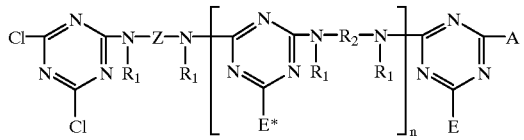

Thereafter, the compounds of the formula (XXX) are caused to react with the appropriate molar amounts of the compounds of the formulae (XV) and/or (XVI) to give the corresponding compounds of the formula (I).

The compounds of the formula (XXV) may be prepared by using well known synthesis processes, for example, by reacting the compound of the formula (IX) with the appropriate molar amounts of the compounds of the formula (XVII).

The various reactions described above are advantageously carried out in an inert organic solvent, for example toluene, xylene or mesitylene, in the presence of an inorganic base such as sodium hydroxide, potassium hydroxide, sodium carbonate or potassium carbonate to neutralize the hydrohalic acid formed during the reactions. Sodium hydroxide is preferred.

The working temperatures of the reactions can vary, for example, from −20° C. to 200° C., preferably from −10° C. to 190° C., in particular from −10° C. to 20° C. for the substitution of the first chlorine atom of cyanuric chloride; from 40° C. to 90° C. for the substitution of the second chlorine atom of cyanuric chloride; and from 90° C. to 190° C. for the substitution of the third chlorine atom of cyanuric chloride.

In the above described processes, the reactions among the compounds of the formula (VII), (XX), (XXII), (XXVIII), (XXIX) or (XXX) and the compounds of the formulae (XV) and/or (XVI) may also be carried out in neat. In such a case, the compounds of the formulae (XV) and/or (XVI) are used in a large excess to neutralize the hydrohalic acid formed during the reactions.

The various stages of the reactions can be carried out in a single reactor and in the same reaction medium, without isolating the intermediates or the reactions can be carried out after separation and, where appropriate, purification of the intermediate compounds.

The reagents employed are commercially available or can be prepared in accordance with known processes. The diamine starting materials of the formulae (VIII) and (XXIV) may be prepared, for example, analogously to the method described in EP-A-33 663 and U.S. Pat. No. 4,526,972, taking Chemical Abstracts 72:32 718t, 75:130 747h and 83:194 575y into account.

The compounds of the formula (I) are very effective in improving the light, heat and oxidation resistance of organic materials, especially synthetic polymers and copolymers, in particular polypropylene fibres.

Examples of organic materials which can be stabilized are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).
   b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethyleneloctene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrenelbutadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylenelbutylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.
8. Halogen-containing polymers such as polychloroprene, chlorinated rubbers, chlorinated and brominated copolymer of isobutylene-isoprene (halobutyl rubber), chlorinated or suffochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.
9. Polymers derived from α,β-unsaturated acids and derivatives thereof such as polyacrylates and polymethacrylates; polymethyl methacrylates, polyacrylamides and polyacrylonitriles, impact-modified with butyl acrylate.
10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.
11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.
12. Homopolymers and copolymers of cyclic ethers such as polyalkylene glycols, polyethylene oxide, polypropylene oxide or copolymers thereof with bisglycidyl ethers.
13. Polyacetals such as polyoxymethylene and those polyoxymethylenes which contain ethylene oxide as a comonomer; polyacetals modified with thermoplastic polyurethanes, acrylates or MBS.
14. Polyphenylene oxides and sulfides, and mixtures of polyphenylene oxides with styrene polymers or polyamides.
15. Polyurethanes derived from hydroxyl-terminated polyethers, polyesters or polybutadienes on the one hand and aliphatic or aromatic polyisocyanates on the other, as well as precursors thereof.
16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycole as well as polyamides or copolyamides modified with EPDM or ABS; and polyamides condensed during processing (RIM polyamide systems).
17. Polyureas, polyimides, polyamide-imides, polyetherimids, polyesterimids, polyhydantoins and polybenzimidazoles.
18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.
19. Polycarbonates and polyester carbonates.
20. Polysulfones, polyether sulfones and polyether ketones.
21. Crosslinked polymers derived from aldehydes on th e one hand and phenols, ureas and melamines on the other hand, such as phenol/formaldehyde resins, urea/formaldehyde resins and melamine/formaldehyde resins.
22. Drying and non-drying alkyd resins.
23. Unsaturated polyester resin s derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, isocyanates, isocyanurates, polyisocyanates or epoxy resins.
26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PANPPO, PBT/PC/ABS or PBT/PET/PC.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxylated styrene/butadiene copolymers.

The invention thus also relates to a composition comprising an organic material susceptible to degradation induced by light, heat or oxidation and at least one compound of the formula (I).

The organic material is preferably a synthetic polymer, more particularly one selected from the aforementioned groups. Polyolefins are preferred and polyethylene and polypropylene are particularly preferred.

A further embodiment of this invention is a method for stabilizing an organic material against degradation induced by light, heat or oxidation, which comprises incorporating into said organic material at least one compound of the formula (I).

The compounds of the formula (I) can be used in various proportions depending on the nature of the material to be stabilized, on the end use and on the presence of other additives.

In general, it is appropriate to use, for example, 0.01 to 5% by weight of the compounds of the formula (I), relative to the weight of the material to be stabilized, preferably 0.05 to 2% in particular 0.05 to 1%

The compounds of the formula (I) can be added, for example, to the polymeric materials before, during or after the polymerization or crosslinking of the said materials. Furthermore, they can be incorporated in the polymeric materials in the pure form or encapsulated in waxes, oils or polymers.

In general, the compounds of the formula (I) can be incorporated in the polymeric materials by various processes, such as dry mixing in the form of powder, or wet mixing in the form of solutions or suspensions or also in the form of a masterbatch which contains the compounds of the formula (I) in a concentration of 2.5 to 25% by weight; in such operations, the polymer can be used in the form of powder, granules, solutions, suspensions or in the form of latices.

The materials stabilized with the compounds of the formula (I) can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, corrosion inhibitors and metal deactivators, can be added to the organic materials containing the compounds of the formula (I).

Particular examples of said conventional additives are:
1. Antioxidants
1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenoll, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.
1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.
1.3. Hydroquinones and alkylated hydroguinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.
1.4. Tocopherols, for example $\alpha$-tocopherol, 0-tocopherol, y-tocopherol, 8-tocopherol and mixtures thereof (Vitamin E).
1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.
1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butyl-phenol), 2,2'-ethylidenebis(6-tert-butyl-4-isobutylphenol), 2,2'-methylenebis[6-($\alpha$-methylbenzyl)-4-nonylphenol], 2,2'-methylenebis[6-($\alpha,\alpha$-dimethylbenzyl)-4-nonylphenol], 4,4'-methylenebis(2,6-di-tert-butyl phenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadi-1,1-bis-(3,5-dimethyl -2-hydroxyphenyi)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyb) pentane.
1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxy benzyl)amine, bis(4-tert-butyl-3-hydroxy-2,6-dimethylbenzyl)dithioterephthalate, bis (3,5-di-tert-butyl-4-hydroxybenzyl)sulfide, isooctyl-3,5-di-tert-butyl-4-hydroxybenzylmercaptoacetate.
1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, didodecylmercaptoethyl-2,2-bis-(3,5-di-tert-butyl-4-hydroxybenzyl) malonate, bis[4-(1,1,3,3-tetramethylbutyl)phenyl]-2,2-bis(3,5-tert-butyl-4-hydroxybenzyl)malonate.
1.9. Aromatic hydroxybenzyl compounds, for example 1,3,5-tris-(3,5-di-tert-butyl-4-hydroxybenzyl-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.
1.10. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,26-bis (3,5-di-tert-butyl -4-hydroxyphenoxy)-1,3,5-triazine, 2,4, 6-tris(3,5-di-tert-butyl-4-hydroxyphenoxy)-1,2,3-triazine, 1,3,5-tris-(3,5-di-tert-butyl-4-hydroxybenzyl) isocyanurate, 1,3,5-tris(4-tert-butyl-3-hydroxy-2,6-dimethyl ben zyl)isocyanurat e, 2,4,6-tris(3,5-di-tert-butyl-4-hydroxy phenylethyl)-1,3,5-triazine, 1,3,5-tris(3, 5-di-tert-butyl-4-hydroxyphenylpropionyl)-hexahydro-1, 3,5-triazine, 1,3,5-tris(3,5-dicycohexyl-4-hydroxybenzyl) isocyanurate.

1.11. Benzelphosphonates, for example dimethyl-2,5-di-tert-butyl -4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethyl ene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl -1-phospha-2,6,7-trioxabicyclo[2.2.2] octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.15. Esters of β-(3,5-digyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3-thiaundecanol, 3-thiapentadecanol, trim ethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethyloipropane, 4-hydroxymethyl-1-phospha-2,6,7-trioxabicyclo[2.2.2] octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl)-hydrazide, N,N'-bis[2-(3-[3,5-di-tert-butyl-4-hydroxyphenyl]propionyloxy)ethyl] oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl—N'-phenyl-p-phenylenediamine, N-(1,3-dimethylbutyl)-N'-phenyl-p-phenylenediamine, N-(1-methylheptyl)—N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-(4-tert-octylphenyl)-1-naphthylamine, N-phenyl-2-naphthylamine, octylated diphenylamine, for example p,p'-di-tert-octyidiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)aminolethane, 1,2-bis (phenylamino)propane, (α-tolyl)biguanide, bis[4-(1',3'-dimethylbutyl)phenyl]amine, tertoctylated N-phenyl-1-naphthylamine, a mixture of mono- and dialkylated tert-butyl/tertoctyidiphenylamines, a mixture of mono- and dialkylated nonyidiphenylamines, a mixture of mono- and dialkylated dodecyidiphenylamines, a mixture of mono- and dialkylated isopropyl/isohexyidiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis-( 2,2,6,6-tetramethyl-piperid-4-yl-hexamethylenediamine, bis(2,2,6,6-tetramethylpiperid-4-yl)-sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl) phenyl) benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, hydroxy-4'-octyloxyphenyl)benzotriazole, 2-(3',5'-di-tert-amyl-2'-hydroxyphenyr)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl) phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl) phenyl)benzotriazole, 2-(3'-tert-butyl-2'-hydroxy-5'-(2- octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis-[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

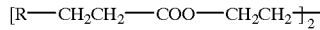

where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl (α-cyano-β,β-diphenylacrylate, isooctyl α-cyano-β,β-diphenylacrylate, methyl (α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tertbutylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tertbutylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis-(2,2,6,6-tetramethyl-4-piperidyl) hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl- 4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino) ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxycarbonyl)-2-(4-methoxyphenyi)ethene, N,N'-bisformyl-N,N'-bis(2,2,6,6-tetramethyl-4-piperidyl) hexamethylenediamine, diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hvdroxyphenyl)-1,3,5-triazines, for example 2,4, 6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis-(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4- dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3 -butoxy-2-hydroxy-propoxy) phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal—N'-salicyloyl hydrazine, N,N'-bis (salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenythydrazide, N,N'-diacetyladipoyl dihydrazide, N,N'-bis(salicyloyl)oxalyl dihydrazide, N,N'-bis (salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2, 4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,1 0-tetra-tert-butyl-1 2H-di-benz[d, g]-1,3,2-dioxaphosphocin, 6-fluoro-2,4,8,10-tetra-tert-butyl-1 2-methyl-dibenz[d,g]-1,3,2-dioxaphosphocin, bis (2,4-di-tert-butyl-6-methylphenyl) methyl phosphite, bis (2,4-di-tert-butyl-6-methylphenyl) ethyl phosphite, 2,2', 2"-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1 '-biphenyl-2,2'-di-yl)phosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercapto-benzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216, 052; U.S. Pat. No. 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl]benzofuran-2-one, 3,3'-bis[5, 7-di-tert-butyl-3-(4-[2-hydroxyethoxy]phenyl) benzofuran-2-one), 5,7-di-tert-butyl-3-(4-ethoxyphenyl) benzofuran-2-one, 3-(4-acetoxy-3,5-dimethylphenyl)-5, 7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The weight ratio of the compounds of the formula (I) to the conventional additives may be for example 1:0.5 to 1:5.

The compounds of the formula (I) can also be used as stabilizers, especially as light stabilizers, for almost all materials known in the art of photographic reproduction and other reproduction techniques as e.g. described in Research Disclosure 1990, 31429 (pages 474 to 480).

The invention is illustrated in more detail by the following Examples. All percentages are by weight, unless otherwise indicated. The compounds of the following Examples 1, 2, 3, 4 and 8 are of particular interest.

EXAMPLE 1

A) Preparation of N,N'-bis(2,2,6,6-tetramethyl-4-piperidyl)-1,3-pentanediamine.

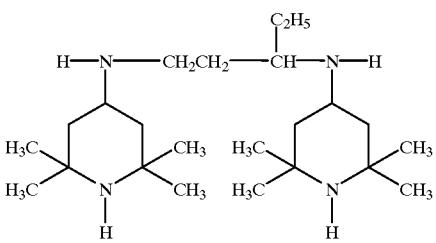

A solution of 80.7 g (780 mmol) of 1,3-pentanediamine and 220 g (1417 mmol) of 2,2,6,6-tetramethyl-4-piperidone in 250 ml of ethanol is heated to 80° C. The reaction mixture is maintained, under stirring, at 80° C. for 2 hours.

Then, the solution is poured into an autoclave, added with 4 g of 5% Pt/C (% w/w) and the autoclave is pressurized with hydrogen.

The mixture is heated to 60° C. and the pressure is maintained at 40 bars for 20 hours. Then, the mixture is cooled to room temperature, filtered and the solvent is evaporated in vacuo (40° C./1 mbar). The oil residue is distilled off.

The product obtained has a boiling point of 160° C./0.1 mbar.

B) Preparation of the compound of the formula

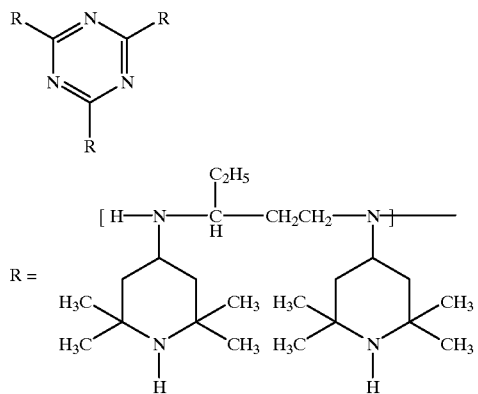

A solution of 8.1 g (44 mmol) of cyanuric chloride in 80 ml of xylene is slowly added to a solution, cooled to –10° C., of 50 g (131 mmol) of N,N'-bis(2,2,6,6-tetramethyl-4-piperidyl)-1,3-pentanediamine in 500 ml of xylene.

After the addition, the mixture is heated to 0° C. and a solution of 5.8 g (144 mmol) of sodium hydroxide in 12 ml of water is added. Then, the mixture is heated to room temperature and is maintained at this temperature for 1 hour under stirring. Subsequently, the mixture is heated to reflux, being the added water and the reaction water distilled off by azeotropation. Then, the mixture is heated to 170° C., by distilling off 300 ml of xylene. The mixture is maintained at 170° C. for 3 hours. Then, the mixture is cooled to room temperature and washed twice with 50 ml of water. The organic phase is separated off, dried over anhydrous sodium sulfate, filtered and evaporated in vacuo (50° C./1 mbar).

The melting point of the product obtained is 75°–79° C.

| Analysis for $C_{72}H_{141}N_{15}$: | | | |
|---|---|---|---|
| Calculated: | C: 71.06% | H: 11.68% | N: 17.26% |
| Found: | C: 70.02% | H: 11.45% | N: 17.09% |

$^1$H NMR (300 MHz, CDCl$_3$):
δ 2.6 ppm (broad, 3H 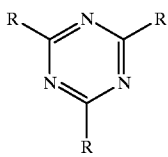 ).

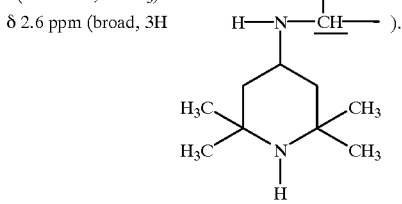

C) Preparation of the compound of the formula

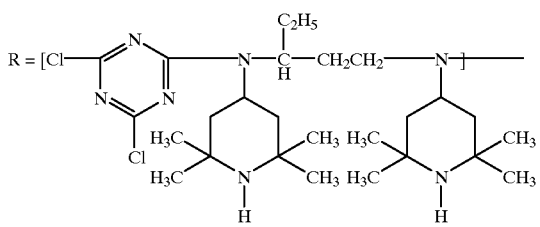

A solution of 24.1 g (130 mmol) of cyanuric chloride in 240 ml of xylene is slowly added to a solution, cooled to 0° C., of 54.3 g (43 mmol) of the compound prepared according to B) in 200 ml of xylene. After the addition, the mixture is stirred at room temperature for 20 hours. Then, a solution of 5.2 g (130 mmol) of sodium hydroxide in 20 ml of water is added. The mixture is maintained at room temperature for 2 hours under stirring. Then, the mixture is washed twice with 100 ml of water, dried over anhydrous sodium sulfate, filtered and evaporated in vacuo (40° C/1 mbar).

| Cl analysis: | |
|---|---|
| Calculated: | Cl: 12.81% |
| Found: | Cl: 12.70% |

D) Preparation of the compound of the formula

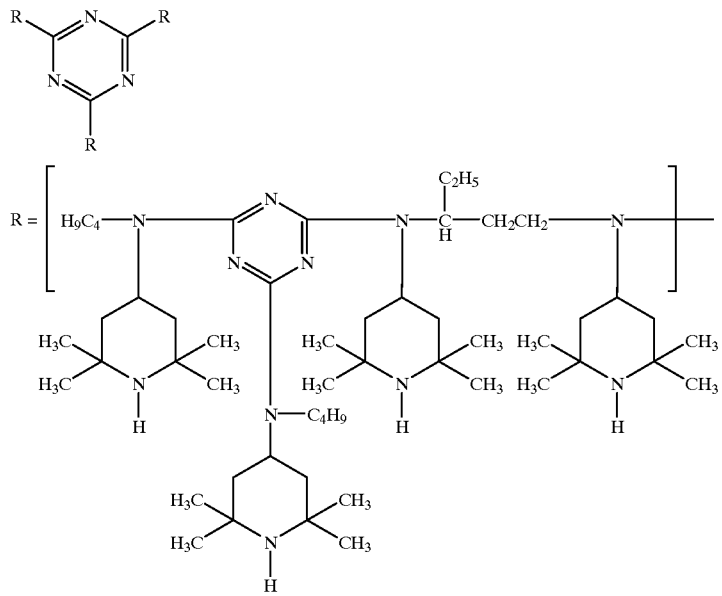

A mixture of 23 g (14 mmol) of the compound prepared according to C) in 126 g (593 mmol) of N-(2,2,6,6-tetramethyl-4-piperidyl)butylamine is heated to 180° C. The reaction mixture is maintained at 180° C. for 5 hours. Then, the mixture is cooled to 60° C. and 230 ml of xylene are added. A solution of 6.7 g (166 mmol) of sodium hydroxide in 40 ml of water is added. The aqueous phase is separated off and the organic solution is washed twice with 100 ml of water, dried over sodium sulfate, filtered and evaporated in vacuo (70° C/1 mbar).

The melting point of the product obtained is 184°–194° C.

| Analysis for $C_{166}H_{304}N_{36}$: | | | |
|---|---|---|---|
| Calculated: | C: 70.35% | H: 11.06% | N: 18.58% |
| Found: | C: 69.59% | H: 10.88% | N: 18.14% |

EXAMPLE 2

Preparation of the compound of the formula

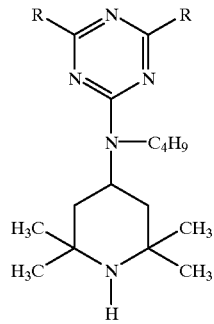

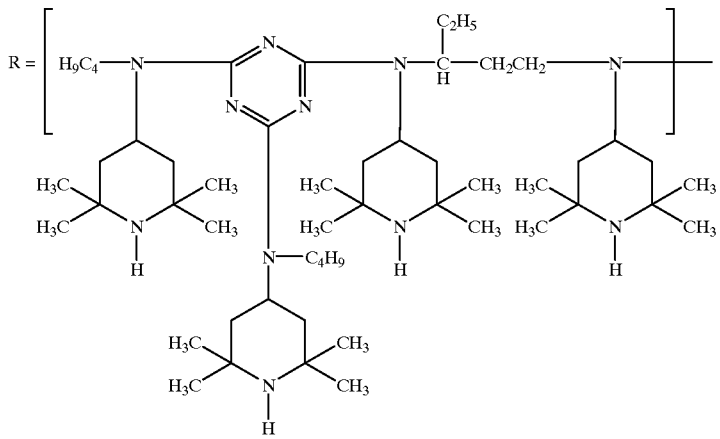

A solution of 37 g (201 mmol) of cyanuric chloride in 370 ml of toluene is slowly added to a solution, cooled to −10° C., of 153 g (401 mmol) of N,N'-bis(2,2,6,6-tetramethyl-4-piperidyl)-1,3-pentanediamine in 1100 ml of toluene. During the addition, the temperature is maintained at −10° C. Subsequently, the mixture is heated to room temperature and maintained, under stirring, at room temperature for 3 hours.

Then, the mixture is cooled to 0° C. and a solution of 32 g (802 mmol) of sodium hydroxide in 64 ml of water is added. After the addition, the mixture is heated again to room temperature, maintained, under stirring, at room temperature for 12 hours, heated to 80° C. and maintained at 80° C. for 3 hours.

Then, the mixture is cooled to room temperature, being the aqueous phase separated off.

A solution of 74.1 g (402 mmol) of cyanuric chloride in 700 ml of toluene is slowly added to the mixture, cooled to 0° C.

After the addition, the mixture is heated to room temperature and maintained at room temperature, under stirring, for 24 hours.

A solution of 16.1 g (402 mmol) of sodium hydroxide in 75 ml of water is added, being the mixture stirred at room temperature for further 4 hours. Then, the aqueous phase is separated off, the organic phase is washed twice with 100 ml of water and toluene is evaporated in vacuo (70° C./1 mbar).

Subsequently, 1344 g (6.3 mol) of N-(2,2,6,6-tetramethyl-4-piperidyl)butylamine are added and the mixture is heated to 180° C. and maintained at 180° C., under stirring, for 5 hours. The mixture is cooled to 60° C. and 300 ml of toluene are added. A solution of 60 g (1.50 mol) of sodium hydroxide in 150 ml of water is added and, after stirring, the aqueous phase is separated off. The organic solution is washed twice with 200 ml of water, dried over anhydrous sodium sulfate, filtered and evaporated in vacuo (70° C./1 mbar).

The melting point of the product obtained is 173°–178° C.

| Analysis for $C_{120}H_{227}N_{27}$: | | | |
|---|---|---|---|
| Calculated: | C: 70.42% | H: 11.10% | N: 18.48% |
| Found: | C: 70.01% | H: 11.07% | N: 18.21% |

EXAMPLE 3

Preparation of the compound of the formula

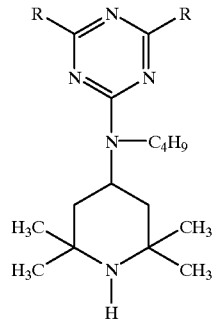

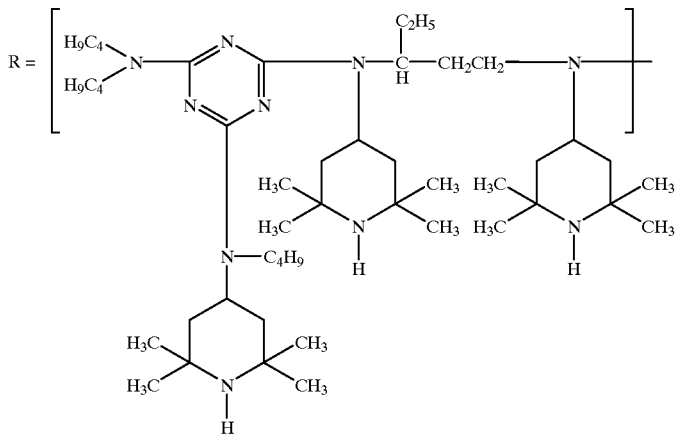

A solution of 36.8 g (200 mmol) of cyanuric chloride in 370 ml of toluene is slowly added to a solution, cooled to −10° C., of 153 g (401 mmol) of N,N'-bis(2,2,6,6-tetramethyl-4-piperidyl)-1,3-pentanediamine in 1100 ml of toluene. During the addition, the temperature is maintained at −10° C. Then, the mixture is heated to room temperature and maintained, under stirring, at room temperature for 3 hours. The mixture is cooled to 0° C. and a solution of 32 g (800 mmol) of sodium hydroxide in 64 ml of water is added. After the addition, the mixture is stirred for 12 hours at room temperature, heated to 80° C. and maintained at 80° C. for 3 hours. Subsequently, the mixture is cooled to room temperature, being the aqueous phase separated off. A solution of 73.8 g (400 mmol) of cyanuric chloride in 690 ml of toluene is slowly added to the organic mixture cooled to 0° C. Then, the mixture is heated to room temperature and maintained under stirring at the above temperature for 24 hours. A solution of 16 g (400 mmol) of sodium hydroxide in 75 ml of water is added and the mixture is stirred at room temperature for further 4 hours. The aqueous phase is separated off and the organic phase is washed twice with 100 ml of water.

Then, a solution of 51.7 g (400 mmol) of dibutylamine in 100 ml of toluene is slowly added and, after 1 hour of stirring at room temperature, a solution of 32 g (800 mmol) of sodium hydroxide in 100 ml of water is added. Subsequently, the mixture is heated to 80° C. for 2 hours, cooled again to room temperature and the aqueous phase is separated off. The organic phase is washed twice with 100 ml of water and toluene is evaporated in vacuo (70° C./1 mbar).

The residue is taken up with 1560 g (7.3 mol) of N-(2,2,6,6-tetramethyl-4-piperidyl)-butylamine and heated to 180° C. Then, the mixture is maintained under stirring at 180° C. for 5 hours. After cooling to 60° C., 800 ml of toluene are added. Then, a solution of 24 g (600 mmol) of sodium hydroxide in 130 ml of water are added and the aqueous phase is separated off. After washing twice with 300 ml of water, the organic phase is dried over anhydrous sodium hydroxide, filtered and evaporated in vacuo (70° C/1 mbar).

The product obtained has a melting point of 132°–139° C.

| Analysis for $C_{110}H_{209}N_{25}$: | | | |
|---|---|---|---|
| Calculated: | C: 69.40% | H: 10.95% | N: 19.65% |
| Found: | C: 69.25% | H: 11.09% | N: 19.08% |

EXAMPLE 4

Preparation of the compound of the formula

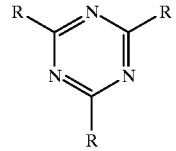

-continued

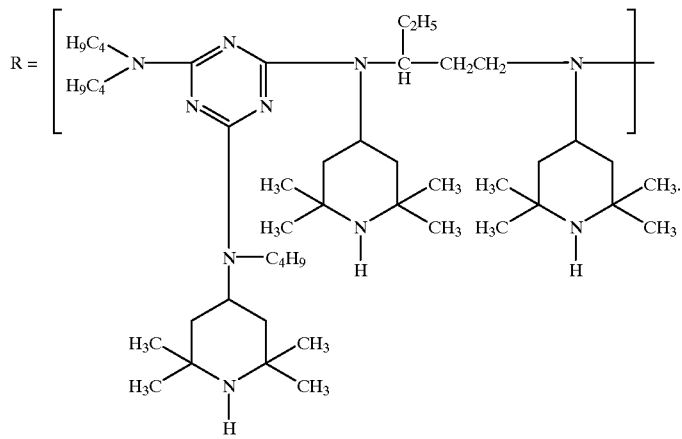

A mixture of 60.1 g (36 mmol) of the compound prepared according to Example 16 in 400 g (3 mol) of N-(2,2,6,6-tetramethyl-4-piperidyl)butylamine is heated to 180° C. and maintained at 180° C. for 5 hours. Then, the mixture is cooled to 60° C. and 200 ml of toluene are added. A solution of 17.2 g (432 mmol) of sodium hydroxide in 100 ml of water are added and the organic phase is separated off.

After washing twice with 200 ml of water, the organic solution is dried over anhydrous sodium sulfate, filtered and evaporated in vacuo (70° C./1 mbar).

The product obtained has a melting point of 148°–152° C.

| Analysis for $C_{144}H_{273}N_{33}$: | | | |
|---|---|---|---|
| Calculated: | C: 70.16% | H: 11.08% | N: 18.76% |
| Found: | C: 69.32% | H: 11.08% | N: 18.61% |

EXAMPLE 5

Preparation of the compound of the formula

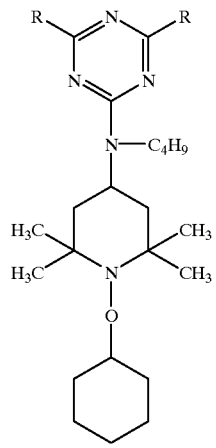

-continued

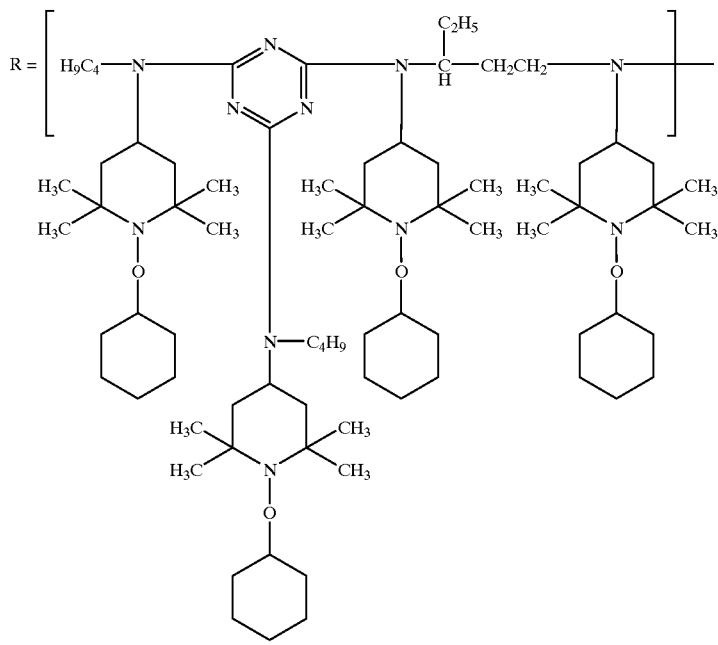

A mixture of 40 g (20 mmol) of the compound of Example 2 in 400 ml of cyclohexane is heated to reflux. Then, 0.2 g of $MoO_3$ is added. 116 g (890 mmol) of 70% (% w/w) aqueous solution of t-butyl hydroperoxide are slowly added. Further 0.2 g of $MoO_3$ are added and the water is distilled off by azeotropation. After the removal of the water, the mixture is heated to 125° C. in a pressure resistant flask and maintained at 125° C. for 4 hours.

Then, the mixture is cooled to 50° C. and $MoO_3$ is filtered off. The organic solution is stirred with a solution of 25 g (190 mmol) of sodium sulfite in 100 ml of water for 1 hour and washed twice with 100 ml of water. Subsequently, the organic solution is dried over anhydrous sodium sulfate, filtered and evaporated in vacuo (40° C./1 mbar).

The product obtained has a melting point of 177°–187° C.

| Analysis for $C_{175}H_{321}N_{27}O_9$: | | | |
|---|---|---|---|
| Calculated: | C: 71.30% | H: 10.83% | N: 12.91% |
| Found: | C: 71.29% | H: 10.90% | N: 12.90% |

EXAMPLE 6

Preparation of the compound of the formula

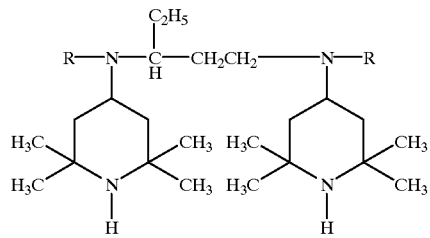

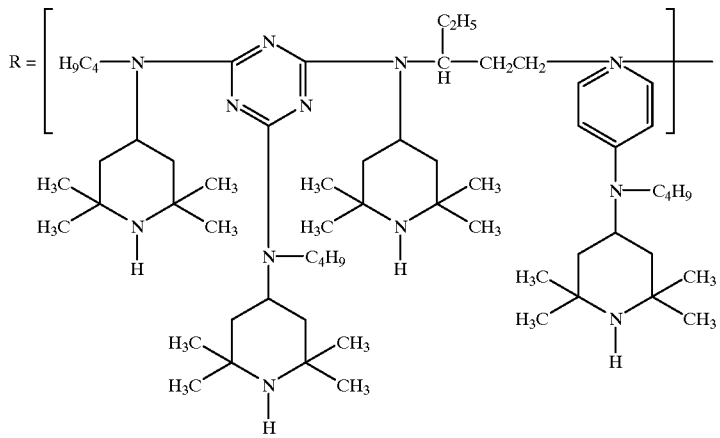

A solution of 5 g (13 mmol) of N,N'-bis(2,2,6,6-tetramethyl-4-piperidyl)-1,3-pentanediamine in 30 ml of toluene is slowly added to a solution, cooled to 0° C., of 4.8 g (26 mmol) of cyanuric chloride in 70 ml of toluene. After the addition, the mixture is heated to room temperature and maintained at room temperature for 1 hour under stirring. Then, the mixture is cooled to 0° C. and a solution of 2 g (42 mmol) of sodium hydroxide in 4 ml of water is added. The mixture is heated again to room temperature, maintained under stirring at room temperature for further 1 hour, being 50 ml of toluene and 10 ml of water added. After stirring for further 10 hours, the organic phase is washed twice with 50 ml of water. A solution of 5.4 g (14 mmol) of N,N'-bis(2,2,6,6-tetramethyl-4-piperidyl)-1,3-pentanediamine in 50 ml of toluene is slowly added to the solution, cooled at 0° C. After the addition, the mixture is heated to room temperature and maintained at room temperature for 1 hour.

Then, a solution of 1.1 g (29 mmol) of sodium hydroxide in 3 ml of water is added and the mixture is heated to 80° C. The mixture is maintained at 80° C. for further 5 hours, under stirring. After cooling to room temperature, the mixture is washed with water. A solution of 2.2 g (12 mmol) of cyanuric chloride in 22 ml of toluene is slowly added to a solution, cooled at 0° C. After the addition, the mixture is heated to room temperature and maintained at room temperature for 14 hours. A solution of 0.5 g (12 mmol) of sodium hydroxide in 1 ml of water is added and the mixture is stirred for 1 hour. After washing twice with 50 ml of water, the organic phase is evaporated in vacuo (40° C./1 mbar) and the residue is taken up with 42.5 g (200 mmol) of N-(2,2,6,6-tetramethyl-4-piperidyl)butylamine. Then, the mixture is heated to 180° C. and maintained at 180° C. for 5 hours under stirring. After cooling to 60° C., a solution of 2.6 g (65 mmol) of sodium hydroxide in 6 ml of water is added. The mixture is stirred for 1 hour, added with 60 ml of toluene, washed twice with 50 ml of water, dried over anhydrous sodium sulfate, filtered and evaporated in vacuo (70° C./1 mbar).

The product obtained has a melting point of 176°–186° C.

| Analysis for $C_{159}H_{300}N_{36}$: | | | |
|---|---|---|---|
| Calculated: | C: 70.35% | H: 11.06% | N: 18.58% |
| Found: | C: 68.59% | H: 10.90% | N: 18.10% |

EXAMPLE 7

Preparation of the compound of the formula

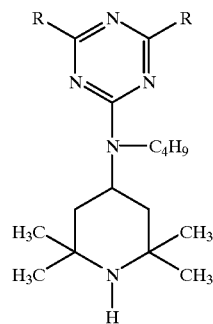

-continued

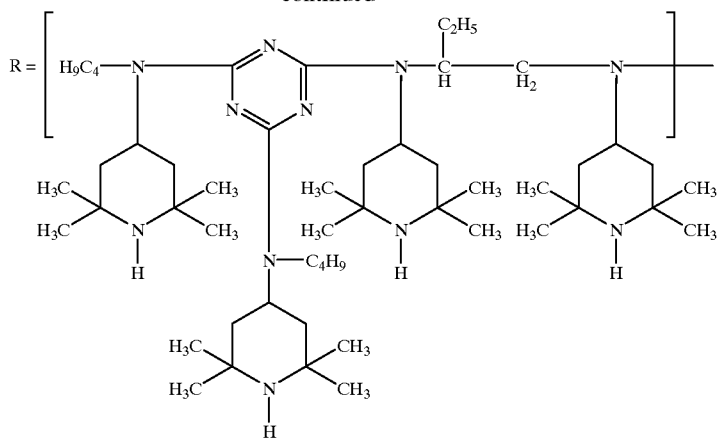

The product is prepared in analogy to the method described in Example 2, using the appropriate reagents in the appropriate molar ratios.

The product obtained has a melting point of 185°–192° C.

| Analysis for $C_{116}H_{219}N_{27}$: | | | |
|---|---|---|---|
| Calculated: | C: 69.98% | H: 11.01% | N: 19.00% |
| Found: | C: 68.35% | H: 10.88% | N: 18.70% |

EXAMPLE 8
Preparation of the compound of the formula

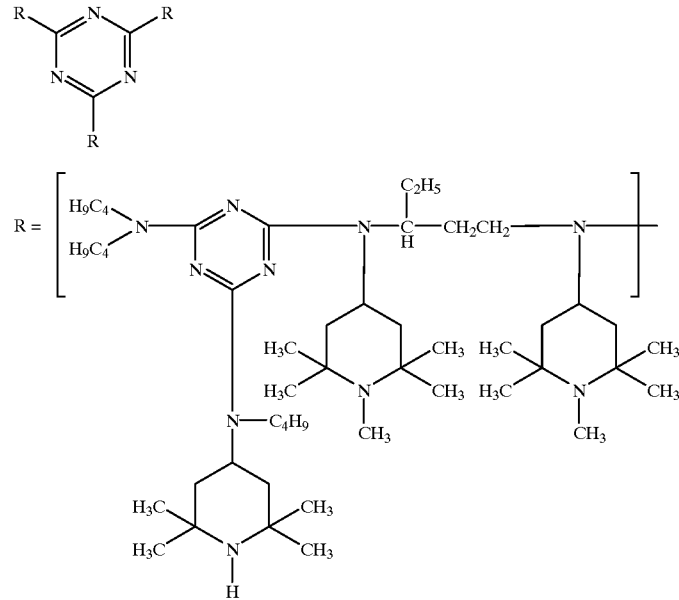

A mixture of 20 g (8.1 mmol) of the compound of Example 4 in 200 ml of t-amyl alcohol and 6.6 g (218 mmol) of paraformaldehyde is heated under stirring to 80° C. Then, 4.3 g (93 mmol) of formic acid is added over a 15 minutes period and left to react for 2 hours. The mixture is cooled down to 25° C. and a solution of 4.46 g (111 mmol) of sodium hydroxide in 50 ml of water is added under stirring and left to react for 30 minutes. The organic layer is washed with water until neutrality. The solvent is evaporated in vacuo (50° C./1 mbar) and 19.5 g of a pale yellow solid is obtained.

The melting point is 165°–175° C.

Analysis for $C_{153}H_{291}N_{33}$:

Calculated:
C: 70.92%
H: 11.80%
N: 17.84%
Found:
C: 70.16%
H: 11.24%
N: 17.50%

EXAMPLE A

Light-stabilizing action in polypropylene fibres.

2.5 g of the stabilizer shown in Table 1, 1 g of tris(2,4-di-tert-butylphenyl) phosphite, 1 g of calcium monoethyl-3,5-di-tert-butyl-4-hydroxybenzyl phosphonate, 1 g of calcium stearate and 2.5 g of titanium dioxide are mixed in a slow mixer with 1000 g of polypropylene powder having a melt index of 12 g/10 min (measured at 230° C. and 2.16 kg).

The mixtures are extruded at 200–230° C. to obtain polymer granules which are then converted into fibres using a pilot-type apparatus (®Leonard-Sumirago (VA); Italy) and operating under the following conditions:
Extruder temperature: 230–245° C.
Head temperature: 255–260° C.
Draw ratio: 1:3.5
Linear density: 11 dtex per filament The fibres prepared in this way are exposed, after mounting on a white cardboard, in a 65 WR Weather-O-Meter (ASTM D2565-85) with a black panel temperature of 63° C.

For samples taken after various times of exposure to the light, the residual tenacity is measured using a constant-speed-tensometer and the exposure time in hours needed to halve the initial tenacity ($T_{50}$) is then calculated.

For purposes of comparison, fibres prepared under the same conditions as described above but without adding the stabilizers of the present invention, are also exposed.

The results are shown in Table 1.

TABLE 1

| Stabilizer | $T_{50}$ (hours) |
|---|---|
| Without stabilizer | 250 |
| Compound of Example 1 | 2030 |
| Compound of Example 2 | 2230 |
| Compound of Example 3 | 1940 |
| Compound of Example 4 | 2030 |
| Compound of Example 7 | 2720 |
| Compound of Example 8 | 1860 |

EXAMPLE B

Light-stabilizing action in polypropylene tapes. 1 g of the stabilizer shown in Table 2, 1 g of tris(2,4-di-tert-butylphenyl) phosphite, 0.5 9 of pentaerythritol-tetrakis(3-(3,5-di-tert-butyl-4-hydroxyphenyl) propionate] and 1 g of calcium stearate are mixed in a turbomixer with 1000 g of polypropylene powder having a melt index of 2.1 g/10 mi (measured at 230° C. and 2.16 kg).

The mixtures are extruded at 200–220° C. to give polymer granules which are subsequently converted to stretched tapes of 50 am thickness and 2.5 mm width, using a semi-industrial type of apparatus (®Leonard-Sumirago (VA)-Italy) and working under the following conditions:
Extruder temperature: 210–230° C.
Head temperature: 240–260° C.
Stretch ratio: 1:6

The tapes, thus prepared, are mounted on a white card and exposed in a Weather-O-Meter 65 WR (ASTM D2565-85) with a black panel temperature of 63° C.

The residual tenacity is measured, by means of a constant velocity tensometer, on a sample taken after various light exposure times; from this, the exposure time (in hours) required to halve the initial tenacity ($T_{50}$) is measured.

By way of comparison, tapes prepared under the same conditions as indicated above, but without the addition of the stabilizers of the present invention, are exposed.

The results obtained are shown in Table 2.

TABLE 2

| Stabilizer | $T_{50}$ (hours) |
|---|---|
| Without stabilizer | 500 |
| Compound of Example 1 | 2090 |
| Compound of Example 2 | 2210 |
| Compound of Example 3 | 2000 |
| Compound of Example 4 | 1980 |
| Compound of Example 7 | 2310 |
| Compound of Example 8 | 1840 |

EXAMPLE C

Antioxidant action in polypropylene plaques.

1 g of each of the compounds listed in Table 3 and 1 g of calcium stearate are mixed in a slow mixer with 1000 g of polypropylene powder having a melt index of 4.3 (measured at 230° C. and 2.16 Kg).

The mixtures are extruded at 220° C. to give polymer granules which are then converted into plaques of 1 mm thickness by injection-moulding at 220° C.

The plaques are then punched using a DIN 53451 mould and the specimens obtained are exposed in a forced circulation air oven maintained at a temperature of 135° C.

The specimens are checked at regular intervals by folding them by 180° in order to determine the time (days) required for fracturing them.

The results obtained are given in Table 3.

TABLE 3

| Stabilizer | Time to fracture (days) |
|---|---|
| Without stabilizer | 10 |
| Compound of Example 1 | 70 |
| Compound of Example 2 | 86 |
| Compound of Example 3 | 67 |
| Compound of Example 4 | 81 |
| Compound of Example 8 | 70 |

EXAMPLE D

Pigment interaction in polypropylene plaques.

5.625 g of the stabilizer shown in Table 4, 13.500 g of Pigment Blue 15 "Flush" (50% mixture in polyethylene) and 25.875 g of polypropylene powder (having a melt index of approximately 14 measured at 230° C. and 2.16 Kg) are added to fill a ®Haake internal mixer at room temperature (®Haake Buchler Rheochord System 40 using a 60 cc 3 piece Rheomixer with cam blades). The cam blades are rotating at 5 RPM (revolutions per minute). A ram closed the bowl under a weight of 5 kg. The temperature is increased to 180° C. and held at 180° C. The total time is 30 minutes.

The mixture is removed while at 180° C. after 30 minutes and cooled down to room temperature. The mixture so obtained—called the "concentrate"—will be used again.

0.900 g of this concentrate, 3.600 g of titanium dioxide "Flush" (50% mixture in polyethylene), and 40.500 g of polypropylene powder (having a melt index of approximately 14 measured at 230° C. and 2.16 Kg) are added to a ®HAAKE mixer bowl at 160° C. The cam blades are rotating at 20 RPM. A ram closes the bowl under a weight of 5 kg. The temperature is increased to 170° C. and the RPM is increased to 125. The total time is 30 minutes.

The molten mixture is removed at 170° C., transferred to a hand held tool at room temperature and transformed into a round plaque 1 mm×25 mm in diameter. The mixture now so obtained is called the "letdown" and the plaque the "letdown plaque."

Color difference, delta E (CIE color difference equation), of sample letdown plaque containing the stabilizer indicated in Table 4 versus control letdown plaque without the stabilizer are measured. The measurement is done using an Applied Color Systems Spectrophotometer Model CS-5 (USA). The measurement parameters used are 400–700 nm—scan, small area view, reflectance, illuminate D65, 10 degree observer.

The above processing conditions are designed to simulate the manufacture of concentrates (masterbatches) of pigments and stabilizers and the subsequent let-down (dilution) into finished plastic articles.

A high delta E indicates pigment agglomeration and poor dispersion. A delta E of 0.5 or less will not be seen as different by the eye.

TABLE 4

| Stabilizer | Delta E |
| --- | --- |
| Compound of Example 2 | 0.2 |

What is claimed is:
1. A compound of the formula (I)

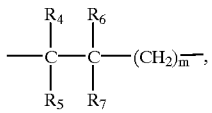

(I)

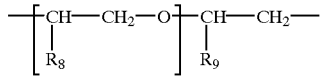

wherein n is 1 or 2;
the radicals $R_1$ are independently of one another hydrogen, $C_1$–$C_8$alkyl, $C_5$–$C_{12}$cycloalkyl unsubstituted or substituted by 1, 2 or 3 $C_1$–$C_4$alkyl; or a group of the formula (II),

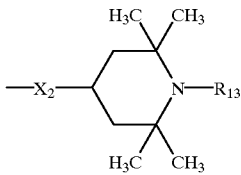

(II)

with the proviso that at least one of the radicals $R_1$ is a group of the formula (II);
$R_3$ is hydrogen, $C_1$–$C_8$alkyl, O·, —OH, —CH$_2$CN, $C_1$–$C_{18}$alkoxy, $C_5$–$C_{12}$cycloalkoxy, $C_3$–$C_6$alkenyl, $C_7$–$C_9$phenylalkyl unsubstituted or substituted on the phenyl by 1, 2 or 3 $C_1$–$C_4$alkyl; or $C_1$–$C_8$acyl;
Z is a group of the formula (IIIa) or (IIIb);

(IIIa)

$$-\overset{R_4}{\underset{R_5}{C}}-\overset{R_6}{\underset{R_7}{C}}-(CH_2)\overline{m}-,$$

(IIIb)

$$-\left[\underset{R_8}{CH}-CH_2-O\right]_p-\underset{R_9}{CH}-CH_2-$$

$R_4$, $R_8$ and $R_9$ are independently of one another $C_1$–$C_4$alkyl or $C_5$–$C_{12}$cycloalkyl unsubstituted or substituted by 1, 2 or 3 $C_1$–$C_4$alkyl;
$R_5$, $R_6$ and $R_7$ are independently of one another hydrogen or $C_1$–$C_4$alkyl;
m is zero or an integer from 1 to 6;
p is 1 or 2;
$R_2$ is a group of formula (IIIa) or is $C_2$–$C_{12}$alkylene, $C_5$–$C_7$cycloalkylene,
$C_5$–$C_7$cycloalkylenedi($C_1$–$C_4$alkylene), $C_1$–C4alkylenedi ($C_5$–$C_7$cycloalkylene), phenylene-di($C_1$–$C_4$alkylene) or $C_4$–$C_{12}$alkylene interrupted by 1,4-piperazinediyl or >N—$X_1$ with $X_1$ being $C_1$–$C_{12}$acyl or ($C_1$–$C_8$alkoxy) carbonyl or having one of the meanings given for $R_1$ except hydrogen;
the radicals A are independently of one another —O$R_{10}$, —N($R_{11}$)($R_{12}$) or a group of the formula (IV);

(IV)

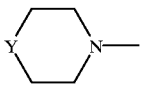

$R_{10}$, $R_{11}$ and $R_{12}$ are independently of one another hydrogen, $C_1$–$C_{12}$alkyl, $C_5$–$C_{12}$cycloalkyl unsubstituted or substituted by 1, 2 or 3 $C_1$–$C_4$alkyl; $C_3$–$C_{12}$alkenyl, phenyl unsubstituted or substituted by 1, 2 or 3 $C_1$–$C_4$alkyl or $C_1$–$C_4$alkoxy; $C_7$–$C_9$phenylalkyl unsubstituted or substituted on the phenyl by 1, 2 or 3 $C_1$–$C_4$alkyl or $C_1$–$C_4$alkoxy; tetrahydrofurfuryl or $C_2$–$C_4$alkyl substituted in the 2, 3 or 4 position by —OH, $C_1$–$C_9$alkoxy or a group of the formula (V)

(V)

$$Y\diagup\diagdown N-$$

with Y being —O—, —CH$_2$—, —CH$_2$CH$_2$— or >N—CH$_3$;
or —N($R_{11}$)($R_{12}$) is additionally a group of the formula (V), with the proviso that Y is not >N—CH$_3$;

$R_{13}$ has one of the meanings given for $R_3$;

$X_2$ is —O— or >N—$R_{14}$;

$R_{14}$ is hydrogen, $C_1$–$C_{12}$alkyl, $C_5$–$C_{12}$cycloalkyl unsubstituted or substituted by 1, 2 or 3 $C_1$–$C_4$alkyl; $C_7$–$C_9$phenylalkyl unsubstituted or substituted on the phenyl by 1, 2 or 3 $C_1$–$C_4$alkyl or $C_1$–$C_4$alkoxy; tetrahydrofurfuryl, a group of the formula (II) or $C_2$–$C_4$alkyl substituted in the 2, 3 or 4 position by —OH, $C_1$–$C_8$alkoxy, di($C_1$–$C_4$alkyl)amino or a group of the formula (V);

the radicals E have independently of one another one of the meanings given for A; and E* has one of the meanings given for A or is a group of the formula (VI)

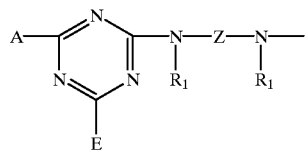

(VI)

with A, E, RI and Z being as defined above;

with the proviso that, when n is 2, each of the radicals E*, $R_1$ and $R_2$ in the repetitive units can have the same or a different meaning.

2. A compound of the formula (I) according to claim 1 wherein $R_3$ is hydrogen, $C_1$–$C_4$alkyl, —OH, $C_6$–$C_{12}$alkoxy, $C_5$–$C_8$cycloalkoxy, allyl, benzyl or acetyl.

3. A compound of the formula (I) according to claim 1 wherein $R_3$ is hydrogen, methyl or cyclohexyloxy.

4. A compound of the formula (I) according to claim 1 wherein

Z is a group of the formula (IIIa); and $R_5$, $R_6$ and $R_7$ are hydrogen.

5. A compound of the formula (I) according to claim 1 wherein the radicals $R_1$ are independently of one another hydrogen, $C_1$–$C_4$alkyl, $C_5$–$C_8$cycloalkyl unsubstituted or substituted by methyl; or a group of the formula (II) with the proviso that at least one of the radicals $R_1$ is a group of the formula (II);

$R_4$, $R_8$ and $R_9$ are independently of one another $C_1$–$C_4$alkyl or cyclohexyl;

$R_5$, $R_6$ and $R_7$ are hydrogen;

m is zero or an integer from 1 to 3;

$R_2$ is a group of the formula (IIIa) or is $C_2$–$C_8$alkylene, cyclohexylene, methylene-cyclohexylene-methylene, cyclohexylene-methylene-cyclohexylene or methylene-phenylene-methylene;

$R_{10}$, $R_{11}$ and $R_{12}$ are independently of one another hydrogen, $C_1$–$C_8$alkyl, $C_5$–$C_8$cycloalkyl unsubstituted or substituted by methyl; $C_3$–$C_8$alkenyl, phenyl unsubstituted or substituted by methyl; benzyl, tetrahydrofurfuryl or $C_2$–$C_3$alkyl substituted in the 2 or 3 position by —OH, $C_1$–$C_4$alkoxy, or 4-morpholinyl; or —N($R_{11}$)($R_{12}$) is additionally 4-morpholinyl;

$R_{14}$ is hydrogen, $C_1$–$C_8$alkyl, $C_5$–$C_8$cycloalkyl unsubstituted or substituted by methyl; benzyl, tetrahydrofurfuryl, a group of the formula (II) or $C_2$–$C_3$alkyl substituted in the 2 or 3 position by —OH, $C_1$–$C_4$alkoxy, dimethylamino, diethylamino or 4-morpholinyl.

6. A compound of the formula (I) according to claim 1 wherein the radicals $R_1$ are independently of one another hydrogen, $C_1$–$C_4$alkyl, cyclohexyl or a group of the formula (II) with the proviso that at least one of the radicals $R_1$ is a group of the formula (II);

Z is a group of the formula (IIIa);

$R_4$ is $C_1$–$C_4$ alkyl;

$R_5$, $R_6$ and $R_7$ are hydrogen;

m is zero or 1;

$R_2$ is a group of the formula (IIIa) or is $C_2$–$C_8$alkylene;

A is —N($R_{11}$)($R_{12}$) or a group of the formula (IV);

$R_{11}$ and $R_{12}$ are independently of one another hydrogen, $C_1$–$C_8$alkyl, cyclohexyl, phenyl, benzyl, tetrahydrofurfuryl, 2-hydroxyethyl or 2-methoxyethyl; or —N($R_{11}$)($R_{12}$) is additionally 4-morpholinyl;

$X_2$ is >N—$R_{14}$;

$R_{14}$ is hydrogen, $C_1$–$C_8$alkyl, cyclohexyl, benzyl, tetrahydrofurfuryl, a group of the formula (II), 2-hydroxyethyl or 2-methoxyethyl.

7. A compound of the formula (I) according to claim 1 wherein n is 1 or 2;

the radicals $R_1$ are a group of the formula (II);

Z is a group

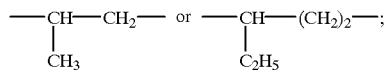

$R_2$ is a group of the formula (IIIa);

$R_3$ is hydrogen, $C_1$–$C_4$alkyl or $C_5$–$C_8$cycloalkoxy;

A is —N($R_{11}$)($R_{12}$) or a group of the formula (IV);

$R_{11}$ and $R_{12}$ are independently of one another $C_1$–$C_4$alkyl;

$X_2$ is >N—$R_{14}$; and $R_{14}$ is $C_1$–$C_4$alkyl.

8. A compound of the formula (I) according to claim 1 which corresponds to the formula

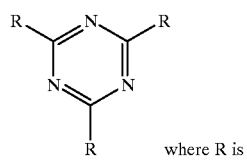 where R is
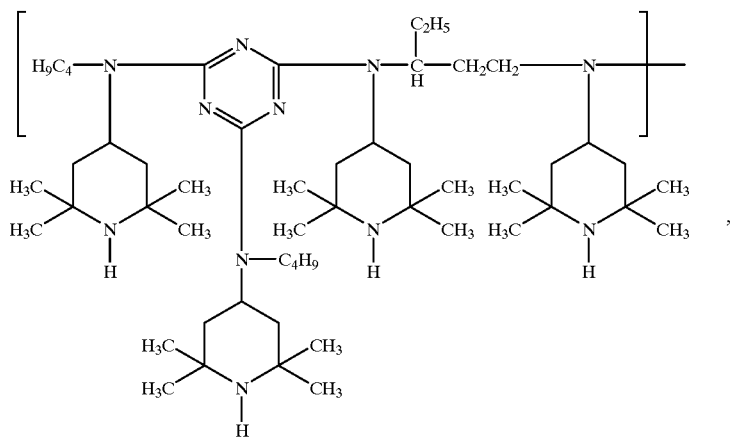,
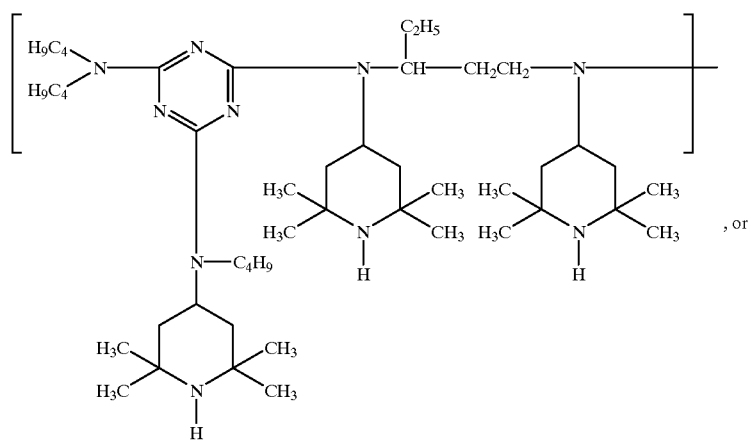, or

-continued
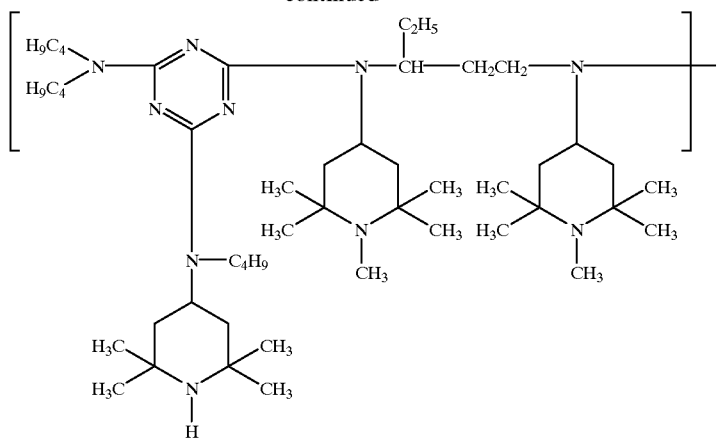
9. A compound of the formula (I) according to claim 1 which corresponds to the formula
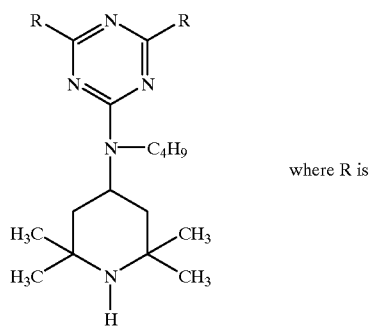
where R is
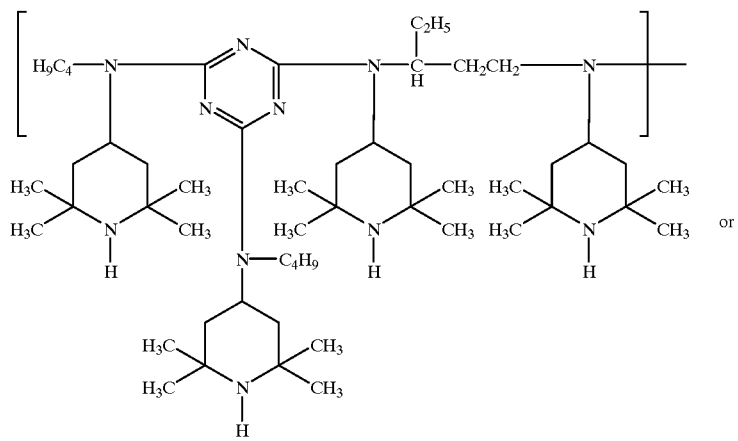
or -continued

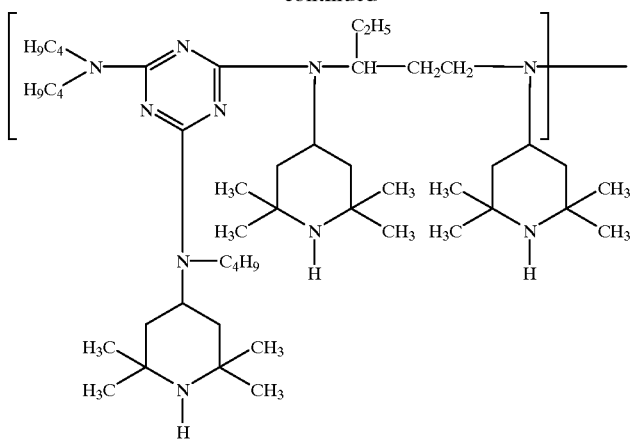

10. A composition containing an organic material susceptible to degradation induced by light, heat or oxidation and at least one compound of the formula (I) according to claim 1.

11. A composition according to claim 10 wherein the organic material is a synthetic polymer.

12. A composition according to claim 10 wherein the organic material is polyethylene or polypropylene.

13. A method for stabilizing an organic material against degradation induced by light, heat or oxidation, which comprises incorporating therein an effective stabilizing amount of at least one compound of the formula (I) according to claim 1.

* * * * *

UNITED STATES PATENT AND TRADEMARK OFFICE
CERTIFICATE OF CORRECTION

PATENT NO. : 6,114,420  
DATED : September 5, 2000  
INVENTOR(S) : Alessandro Zedda et al.

Page 1 of 1

It is certified that error appears in the above-identified patent and that said Letters Patent is hereby corrected as shown below:

ABSTRACT,
Delete lines 2 and 3 (the structure of formula (I)), and
insert --

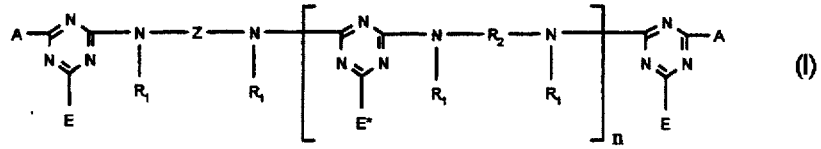

Column 1,
Delete lines 22-35 (structure of formula (I)), and
insert --

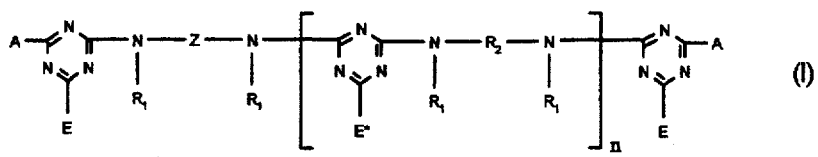

Column 47,
Delete lines 33-34 (structure of formula (I)), and
insert --

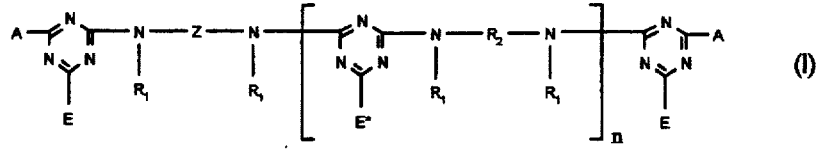

--

Signed and Sealed this

Eleventh Day of December, 2001

Attest:

*Nicholas P. Godici*

NICHOLAS P. GODICI
*Attesting Officer*  *Acting Director of the United States Patent and Trademark Office*